(12) United States Patent
Lobanenkov et al.

(10) Patent No.: US 7,785,814 B2
(45) Date of Patent: Aug. 31, 2010

(54) METHOD OF DETECTING CANCER BASED ON IMMUNE REACTION TO BORIS

(75) Inventors: Victor V. Lobanenkov, Rockville, MD (US); Dmitri Loukinov, Germantown, MD (US); Ziedulla Abdullaev, Damascus, MD (US); Svetlana Pack, N. Potomac, MD (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 165 days.

(21) Appl. No.: 11/575,732

(22) PCT Filed: Sep. 21, 2005

(86) PCT No.: PCT/US2005/033796

§ 371 (c)(1),
(2), (4) Date: Aug. 27, 2007

(87) PCT Pub. No.: WO2006/034335

PCT Pub. Date: Mar. 30, 2006

(65) Prior Publication Data

US 2008/0095805 A1    Apr. 24, 2008

Related U.S. Application Data

(60) Provisional application No. 60/611,798, filed on Sep. 21, 2004.

(51) Int. Cl.
*G01N 33/574* (2006.01)
(52) U.S. Cl. .................................... 435/7.23; 435/7.21
(58) Field of Classification Search ........................ None
See application file for complete search history.

(56) References Cited

U.S. PATENT DOCUMENTS

| 4,281,061 | A | * | 7/1981 | Zuk et al. ..................... 435/7.9 |
| 5,534,254 | A | * | 7/1996 | Huston et al. ............. 424/135.1 |
| 2004/0152877 | A1 | * | 8/2004 | Hillman et al. ............. 530/358 |

FOREIGN PATENT DOCUMENTS

| WO | WO 03/072799 A2 | 9/2003 |
| WO | WO 2005/021029 A2 | 3/2005 |

OTHER PUBLICATIONS

Skolnick et al. (Trends in Biotech., 18(1):34-39, 2000).*
Dong et al., "Identification of two novel CT antigens and their capacity to elicit antibody response in hepatocellular carcinoma patients," *British Journal of Cancer*, 89, 291-297 (2003).
Klenova et al., "The novel *BORIS + CTCF* gene family is uniquely involved in the epigenetics of normal biology and cancer," *Seminars in Cancer Biology*, 12, 399-414 (2002).
Lobanenkov et al., "CTCG and BORIS in Cancer (Epi)genetics," *Keystone Symposia*, 1, (2004).
Loukinov et al., "BORIS, a novel male germ-line-specific protein associated with epigenetic reprogramming events, shares the same 11-zinc-finger domain with CTCF, the insulator protein involved in reading imprinting marks in the soma," *Proc. Natl. Acad. Sci. U.S.A.*, 99(10), 6806-6811 (2002).
Masutomi et al., "Identification of serum anti-human telomerase reverse transcriptase (hTERT) auto-antibodies during progression to hepatocellular carcinoma," *Oncogene*, 21, 5946-5950 (2002).
Rockland Immunochemicals for Research, retrieved from the internet at www.rockland-inc.com/obects/catalog/product/extras/12282_600-401-907.pdf on May 29, 2006, pp. 1-2.

* cited by examiner

*Primary Examiner*—Sheela J Huff
(74) *Attorney, Agent, or Firm*—Leydig, Voit & Mayer, Ltd.

(57) ABSTRACT

The invention provides a method of detecting a proliferative disease, such as a disease associated with the abnormal expression of BORIS, in a mammal comprising detecting antibodies to BORIS in a sample obtained from the mammal. The invention also provides BORIS polypeptides as well as compositions and kits comprising the BORIS polypeptides and methods of using the same. The invention further provides a method of inducing an immune response in a mammal using BORIS polypeptides.

28 Claims, 1 Drawing Sheet

SEQUENCE LISTING

<160> NUMBER OF SEQ ID NOS: 5

<210> SEQ ID NO 1
<211> LENGTH: 778
<212> TYPE: DNA
<213> ORGANISM: Artificial
<220> FEATURE:
<223> OTHER INFORMATION: Synthetic

<400> SEQUENCE: 1

| | | | | | |
|---|---|---|---|---|---|
| atggcagcca | ctgagatctc | tgtcctttct | gagcaattca | ccaagatcaa | agaactcgag | 60 |
| ttgatgccgg | aaaaaggcct | gaaggaggag | gaaaaagacg | gagtgtgcag | agagaaagac | 120 |
| catcggagcc | ctagtgagtt | ggaggccgag | cgtacctctg | gggccttcca | ggacagcgtc | 180 |
| ctggaggaag | aagtggagct | ggtgctggcc | ccctcggagg | agagcgagaa | gtacatcctg | 240 |
| accctgcaga | cggtgcactt | cacttctgaa | gctgtggagt | tgcaggatat | gagcttgctg | 300 |
| agcatacagc | agcaagaagg | ggtgcaggtg | gtggtgcaac | agcctggccc | tgggttgctg | 360 |
| tggcttgagg | aagggccccg | gcagagcctg | cagcagtgtg | tggccattag | tatccagcaa | 420 |
| gagctgtact | ccccgcaaga | gatggaggtg | ttgcagttcc | acgctctaga | ggagaatgtg | 480 |
| atggtggcca | gtgaagacag | taagttagcg | gtgagcctgg | ctgaaactgc | tggactgatc | 540 |
| aagctcgagg | aagagcagga | gaagaaccag | ttattggctg | aaagaacaaa | ggagcagctc | 600 |
| tttttttgtgg | aaacaatgtc | aggagatgaa | agaagtgacg | aaattgttct | cacagtttca | 660 |
| aattcaaatg | tggaagaaca | agaggatcaa | cctacagctg | gtcaagcaga | tgctgaaaag | 720 |
| gccaaatcta | caaaaaatca | agaaagaca | aagggagcaa | aaggaacctt | ccactgtg | 778 |

<210> SEQ ID NO 2
<211> LENGTH: 338
<212> TYPE: DNA
<213> ORGANISM: Artificial
<220> FEATURE:
<223> OTHER INFORMATION: Synthetic

<400> SEQUENCE: 2

| | | | | | |
|---|---|---|---|---|---|
| tggattaacc | tgcacagaca | ttcggagaag | tgtggatcag | gggaagcaaa | gtcggctgct | 60 |
| tcaggaaagg | gaagaagaac | aagaaagagg | aagcagacca | tcctgaagga | agccacaaag | 120 |
| ggtcagaagg | aagctgcgaa | gggatggaag | gaagccgcga | acggagcga | agctgctgct | 180 |
| gaggaggctt | ccaccacgaa | gggagaacag | ttcccaggag | agatgtttcc | tgtcgcctgc | 240 |
| agagaaacca | cagccagagt | caaagaggaa | gtggatgaag | gcgtgacctg | tgaaatgctc | 300 |
| ctcaacacga | tggataagtg | agagggattc | gggttgcg | | | 338 |

<210> SEQ ID NO 3
<211> LENGTH: 1161
<212> TYPE: DNA
<213> ORGANISM: Artificial
<220> FEATURE:
<223> OTHER INFORMATION: Synthetic

<400> SEQUENCE: 3

| | | | | | |
|---|---|---|---|---|---|
| atggcagcca | ctgagatctc | tgtcctttct | gagcaattca | ccaagatcaa | agaactcgag | 60 |
| ttgatgccgg | aaaaaggcct | gaaggaggag | gaaaaagacg | gagtgtgcag | agagaaagac | 120 |
| catcggagcc | ctagtgagtt | ggaggccgag | cgtacctctg | ggccttcca | ggacagcgtc | 180 |
| ctggaggaag | aagtggagct | ggtgctggcc | ccctcggagg | agagcgagaa | gtacatcctg | 240 |

-continued

```
accctgcaga cggtgcactt cacttctgaa gctgtggagt tgcaggatat gagcttgctg      300
agcatacagc agcaagaagg ggtgcaggtg gtggtgcaac agcctggccc tgggttgctg      360
tggcttgagg aagggccccg gcagagcctg cagcagtgtg tggccattag tatccagcaa      420
gagctgtact ccccgcaaga gatggaggtg ttgcagttcc acgctctaga ggagaatgtg      480
atggtggcca gtaagacag taagttagcg gtgagcctgg ctgaaactgc tggactgatc       540
aagctcgagg aagagcagga gaagaaccag ttattggctg aaagaacaaa ggagcagctc      600 tttttttgtgg aaacaatgtc aggagatgaa agaagtgacg aaattgttct cacagtttca    660
aattcaaatg tggaagaaca agaggatcaa cctacagctg gtcaagcaga tgctgaaaag     720
gccaaatcta caaaaaatca aagaaagaca aagggagcaa aaggaacctt ccactgtggg     780
tggcggtggc tccggtggcg gtggctccgg tggcggtggc tcctggatta acctgcacag     840
acattcggag aagtgtggat caggggaagc aaagtcggct gcttcaggaa agggaagaag     900
aacaagaaag aggaagcaga ccatcctgaa ggaagccaca aagggtcaga aggaagctgc     960
gaagggatgg aaggaagccg cgaacggaga cgaagctgct gctgaggagg cttccaccac    1020
gaagggagaa cagttcccag gagagatgtt tcctgtcgcc tgcagagaaa ccacagccag    1080
agtcaaagag gaagtggatg aaggcgtgac ctgtgaaatg ctcctcaaca cgatggataa    1140
gtgagaggga ttcggggttgc g                                              1161
```

```
<210> SEQ ID NO 4
<211> LENGTH: 45
<212> TYPE: DNA
<213> ORGANISM: Artificial
<220> FEATURE:
<223> OTHER INFORMATION: Synthetic

<400> SEQUENCE: 4
ggtggcggtg gctccggtgg cggtggctcc ggtggcggtg gctcc                        45

<210> SEQ ID NO 5
<211> LENGTH: 15
<212> TYPE: PRT
<213> ORGANISM: Artificial
<220> FEATURE:
<223> OTHER INFORMATION: Synthetic

<400> SEQUENCE: 5

Gly Gly Gly Gly Ser Gly Gly Gly Gly Ser Gly Gly Gly Gly Ser
1               5                   10                  15
```

METHOD OF DETECTING CANCER BASED ON IMMUNE REACTION TO BORIS

CROSS-REFERENCE TO RELATED PATENT APPLICATIONS

This application is the U.S. national phase of International Patent Application No. PCT/US05/033796, which was filed on Sep. 21, 2005.

INCORPORATION-BY-REFERENCE OF MATERIAL SUBMITTED ELECTRONICALLY

Incorporated by reference in its entirety herein is a computer-readable nucleotide/amino acid sequence listing submitted on Mar. 21, 2007 and identified as follows: One 4,056 Byte ASCII (Text) file named "701191_SEQUENCE.TXT," created on Mar. 15, 2007.

FIELD OF THE INVENTION

This invention pertains to novel BORIS polypeptides and the use of such polypeptides for the detection of antibodies specific for BORIS in a sample obtained from a mammal. The detection of antibodies in a mammal specific for BORIS is useful, inter alia, for the detection of proliferative diseases, such as cancer.

BACKGROUND OF THE INVENTION

The identification of tumor-associated antigens recognized by a mammalian immune system is useful for the diagnosis and treatment of cancer. A variety of tumor-associated antigens have been identified, including cancer/testis antigens that are expressed in cancer cells, but not in normal tissues other than testis. Only a minority of tumor-associated antigens, however, are immunogenic to the mammal that produces them.

BORIS (Brother of the Regulator of Imprinted Sites) is a tumor-associated antigen, which is activated in a wide range of human cancers. In fact, aberrant synthesis of the BORIS gene product has been found in over 300 primary tumors and cancer cell lines representing all major types of human cancers with recurrent 20q13 chromosomal gains. BORIS activation has also been found in all of the standard NCI-60 cancer cell lines, which are maintained by the National Cancer Institute (NCI), and which are thought to be a reasonably complete representative set of human cancers. One mechanism of action by which BORIS is thought to cause cancer through interference with the maintenance of an appropriate methylation pattern in the genome mediated by CCCTC binding factor (CTCF) (see Klenova et al., *Seminars in Cancer Biology* 12, 399-414 (2002)).

BORIS is also a CTCF paralog, which contains all eleven zinc fingers of CTCF, and has been shown to promote cell growth leading to transformation (see Loukinov et al, *Proc. Natl. Acad. Sci.* (USA) 99, 6806-6811 (2002), and International Patent Application Publication WO 03/072799 (PCT/US03/05186)). The BORIS gene is believed to map to the cancer-associated amplification region of chromosome 20q13.

The detection of aberrant expression of cancer markers, such as prostate specific antigen (PSA) and carcinoembryonic antigen (CEA), are known in the art. These assays, however, detect only a limited number of cancers, and have limited positive predictive value for the detection of new or recurring cancer, or for the prognosis of cancer. Accordingly, there is a need in the art to identify additional antigens whose expression can be linked to hyperproliferative diseases, such as cancer, as well as methods of detecting the presence of such antigens to aid in the detection, diagnosis, prognostication, or research of such disease states.

The invention provides methods and compositions useful for the detection, diagnosis, prognostication, or research of diseases associated with abnormal BORIS expression, such as cancer. These and other advantages of the invention, as well as additional inventive features, will be apparent from the description of the invention provided herein.

BRIEF SUMMARY OF THE INVENTION

The invention provides a method of detecting a disease associated with abnormal BORIS expression, including but not limited to cancer, which method comprises detecting antibodies (e.g., autoantibodies) to BORIS in a sample obtained from a mammal. The invention also provides a method of detecting antibodies to BORIS in a sample obtained from a mammal, which method comprises contacting the sample with a BORIS polypeptide and detecting the presence of antibodies that bind to the BORIS polypeptide.

The invention further provides BORIS polypeptides (e.g., polypeptides comprising BORIS epitopes), compositions, and kits comprising the BORIS polypeptides. In addition, the invention provides a method of inducing an immune response in a mammal comprising administering a BORIS polypeptide to the mammal.

DETAILED DESCRIPTION OF THE INVENTION

Figure 1:
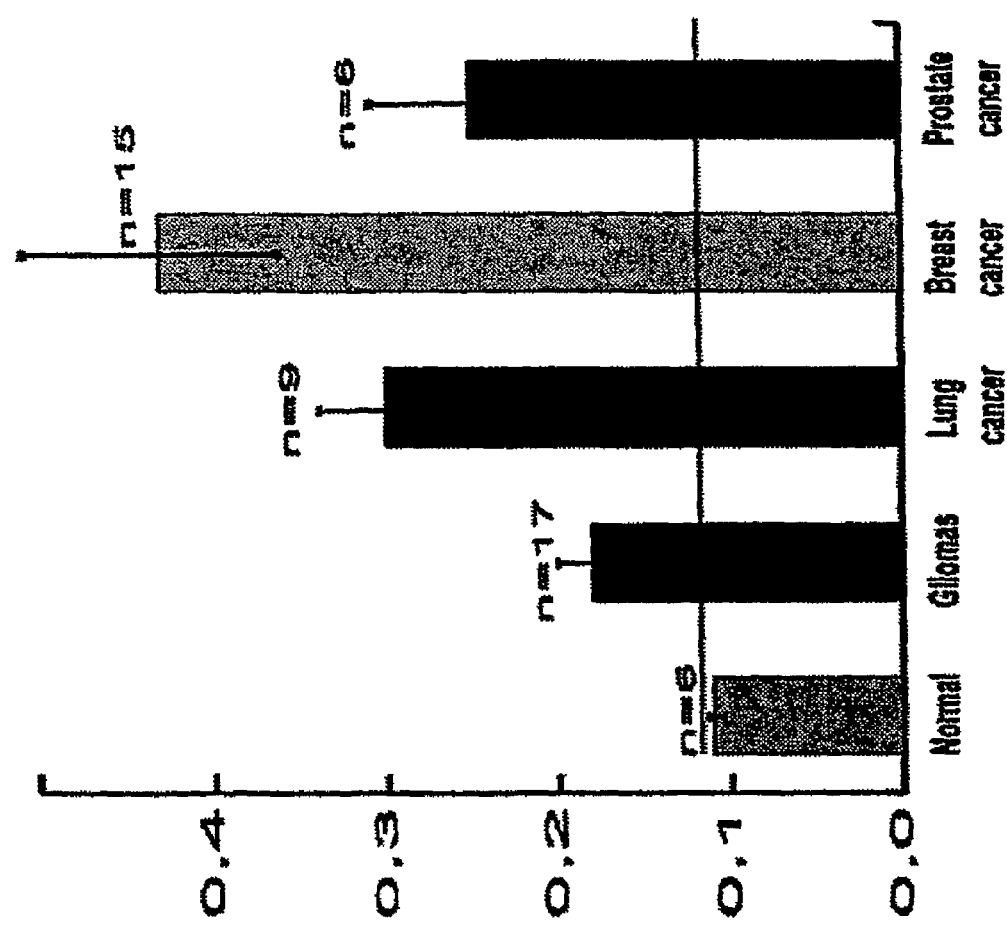
FIG. 1 is a graph depicting results of indirect ELISA assays for anti-BORIS antibodies in human sera.

The invention provides a method of detecting a disease characterized by abnormal gene expression, such as a hyperproliferative disease involving abnormal BORIS expression (e.g., cancer), in a mammal, which method comprises providing a sample from a mammal and detecting antibodies to BORIS in the sample obtained from the mammal. The presence of anti-BORIS antibodies in the sample indicates the presence of the disease in the mammal. The terms "proliferative disease" and "hyperproliferative disease" are used synonymously herein. Without wishing to be bound to any particular theory, it is believed that diseases characterized by abnormal gene expression, such as cancer, are associated with the abnormal expression of BORIS in tissues where BORIS is not normally found (e.g., tissues other than the testes). As a result, the immune system of the mammal produces antibodies to BORIS that can be detected in a sample (e.g., the tissues, sera, or bloodstream) obtained from the diseased mammal. In the absence of such a disease, BORIS is confined to the tissues and organs in which it is normally found (e.g., the testes), and the immune system of the mammal does not produce antibodies against BORIS. Thus, a sample taken from a non-diseased mammal (e.g., a mammal without a disease characterized by abnormal gene expression) will not contain anti-BORIS antibodies. Accordingly, by detecting the presence or absence of anti-BORIS antibodies in the sample of a mammal, the method of the invention enables a determination as to whether the mammal has a disease characterized by abnormal gene expression, especially abnormal BORIS expression, such as cancer.

The terms "BORIS" and "native BORIS" are used synonymously herein to refer to the BORIS polypeptide as found in nature (e.g., as produced by or isolated from a non-genetically engineered mammal). Thus, these terms encompass any natural isoforms or homologues of BORIS. The terms "anti-BORIS antibody" and "antibodies to BORIS" are used synonymously herein to refer to any antibody that binds to BORIS, including autoantibodies to BORIS.

The method of the invention can be used to detect any disease characterized by or associated with the abnormal production of BORIS, and consequent production of anti-BORIS antibodies, including, but not limited, to the detection of cancer. As mentioned above, BORIS mRNA has been detected in several hundred cancer and tumor cell lines representing most of the major forms of cancer. Thus, the method of the invention can be used to detect any type of cancer. Such cancers include, but are not limited to, cancer of the oral cavity and pharynx, the digestive system (e.g., the esophagus, stomach, small intestine, colon, rectum, anus, liver, gall bladder, and pancreas), the respiratory system (e.g., the larynx, lung, and bronchus, including non-small cell lung carcinoma), bones and joints (e.g., bony metastases), soft tissue, the skin (e.g., melanoma), breast, the genital system (e.g., the uterine cervix, uterine corpus, ovary vulva, vagina, prostate, testis, and penis), the urinary system (e.g., the urinary bladder, kidney, renal pelvis, and ureter), the eye and orbit, the brain and nervous system (e.g., glioma), or the endocrine system (e.g., thyroid). The cancer also can be a lymphoma (e.g., Hodgkin's disease and Non-Hodgkin's lymphoma), multiple myeloma, or leukemia (e.g., acute lymphocytic leukemia, chronic lymphocytic leukemia, acute myeloid leukemia, chronic myeloid leukemia, and the like).

Any suitable sample can be used in the invention. The types of samples that can contain antibodies (e.g., autoantibodies) are known in the art. The sample can be a solid sample, such as a tissue sample, or the sample can be fluid, such as a sample of body fluid. For instance, a section of whole tissue can be used for immunohistochemistry-based analysis or can be homogenized to liquefy the components found in the tissue. The sample is preferably a fluid. Suitable fluid samples include, but are not limited to, blood, serum, plasma, lymph, and interstitial fluid.

Any suitable method of detecting anti-BORIS antibodies in a sample can be used. Methods for detecting the presence of antibodies to a known antigen in a sample are available in the art.

In a related aspect, the invention provides a method of detecting antibodies specific for BORIS in a sample obtained from a mammal, which method comprises contacting the sample with a BORIS polypeptide (e.g., a polypeptide comprising a suitable portion of BORIS that comprises one or more BORIS epitopes) and detecting whether the sample contains anti-BORIS antibodies. Of course, the binding of the BORIS polypeptide to an antibody in the sample indicates the presence of anti-BORIS antibodies in the sample. The method of detecting anti-BORIS antibodies can be used for any suitable purpose, and is especially useful for detecting, prognosticating, monitoring, or researching diseases characterized by abnormal gene expression, especially abnormal BORIS expression, including without limitation hyperproliferative diseases such as cancer. Accordingly, the method of detecting anti-BORIS antibodies provided by the invention can be used in conjunction with the method of detecting a disease provided by the invention.

In this regard, the term "BORIS polypeptide" as used herein is defined as a polypeptide to which an anti-BORIS antibody binds. Thus, the term "BORIS polypeptide" as defined for the purposes of this invention encompasses, but is not limited to, native BORIS. As discussed in greater detail below, a BORIS polypeptide can, for example, comprise, consist essentially of, or consist of BORIS, a portion or fragment of BORIS recognized by an anti-BORIS antibody, or a variant of BORIS or portion or fragment thereof recognized by an anti-BORIS antibody.

The BORIS polypeptide can comprise, consist essentially of, or consist of the native BORIS protein or a portion thereof. Full-length BORIS proteins' are known in the art and disclosed, for example, in Loukinov et al., supra, Klenova et al., supra, and GenBank Accession No. AF336042. Other isoforms, homologs, and paralogs can be isolated using the information provided herein and routine techniques.

Any suitable portion of BORIS can be used to detect antibodies specific for BORIS. As used herein, the term "portion" is synonymous with the term "fragment" both of which are used to refer to contiguous part of a polypeptide, preferably comprising 5 or more amino acids. The portion of BORIS can be provided by the full length BORIS protein (e.g., the full-length native BORIS polypeptide); however, in some embodiments it is convenient to use a shorter portion of BORIS. Accordingly, the portion of BORIS can be any portion of the full-length native BORIS protein that can recognize and bind to an anti-BORIS antibody in vitro or in vivo. One can determine whether any given portion of BORIS binds to an anti-BORIS antibodies using routine techniques in view of the disclosures provided herein. For example, anti-BORIS antibodies can be obtained from a mammal using native BORIS. Subsequently, the given "test" portion of BORIS can be contacted with the anti-BORIS antibodies to determine whether the anti-BORIS antibodies bind to the given "test" portion of BORIS. Other methods of determining whether a given portion of BORIS can bind to an anti-BORIS antibody will be apparent to those of ordinary skill in the art.

Suitable portions of BORIS include the amino-terminal portion of BORIS (the "N-terminal domain"), defined as the region extending from the amino-terminal up to the zinc finger domain (the "N-terminal domain"), or at least some portion thereof comprising about 100 or more amino acids (e.g., 200 or more, 250 or more, 300 or more, 400 or more, or 500 or more amino acids) of the BORIS N-terminal domain. A preferred portion of BORIS is the N-terminal domain of BORIS encoded by a nucleic acid sequence comprising, consisting of, or consisting essentially of SEQ ID NO: 1.

Other suitable portions of BORIS include the carboxyl-terminal portion of BORIS, defined as the region starting after the zinc-finger domain and terminating at the carboxyl-terminus of BORIS (the "C-terminal domain"), or at least some portion thereof comprising about 75 or more amino acids (e.g., about 100 or more, 200 or more, 300 or more, or 400 or more amino acids) of the BORIS C-terminal domain. A preferred portion of BORIS includes the C-terminal domain encoded by a nucleic acid sequence comprising, consisting essentially of, or consisting of SEQ ID NO: 2.

In a particularly preferred embodiment of the invention, the BORIS polypeptide comprises at least a portion of each of the N-terminal domain and the C-terminal domain, as described herein. More preferably, the BORIS polypeptide comprises the entire N-terminal domain and C-terminal domain. It is further preferred that the BORIS polypeptide excludes the zinc finger domain. A preferred BORIS polypeptide is encoded by a nucleic acid sequence comprising, consisting of, or consisting essentially of SEQ ID NO: 3.

Even smaller portions of BORIS can be used, provided that a BORIS epitope is present in the portion or fragment. By "epitope" is meant a sequence on an antigen that is recognized by an antibody or an antigen receptor. Epitopes also are referred to in the art as "antigenic determinants." For example, the portion of BORIS, or the BORIS polypeptide comprising, consisting essentially of, or consisting of the portion of BORIS, can be less than about 660, 200, 150, 100, 60, 50, 30, 20, 15, or 12 amino acid residues in length, so long as it can be specifically bound by an antibody that binds to BORIS, and preferably an antibody that binds only to BORIS (i.e., a "BORIS-specific" antibody). The BORIS polypeptide preferably comprises at least about 10, 11, or 12 amino acids. Of course, the preferred number of amino acids also can be expressed in terms of ranges within any of the above described preferred limits (e.g., 10-200 amino acids, 10-100 amino acids, 10-50 amino acids, 10-20 amino acids, etc.). However, BORIS polypeptides comprising fewer than 11 amino acids (e.g., about 4, 6, 8, or 10 or more amino acids) are also within the scope of the invention.

Any epitope of BORIS that is reactive with an anti-BORIS antibody can be used alone, in the context of a larger BORIS polypeptide, inserted into another (i.e., "non-BORIS") protein, or attached to another (i.e., "non-BORIS") protein. Alternatively, more than one BORIS epitope can be used. While not desiring to be bound by any particular theory, it is believed that different individuals will have immunogenic responses to BORIS based on the MHC molecules expressed on their antigen presenting cells (e.g., macrophages). Accordingly, the reactive epitopes of BORIS can vary from individual to individual. Moreover, an autoreactive antibody response directed against both the N-terminal and C-terminal domains of BORIS has been detected in some cancer patients. Thus, the method preferably involves the use of more than one BORIS epitope. When more than one BORIS epitope is used, the different BORIS epitopes can be provided, for example, by several discontiguous portions of BORIS used simultaneously (e.g., two or more BORIS polypeptides each comprising a different portion of BORIS) or linked together and used as a single reagent (e.g., a single BORIS polypeptide comprising two or more different portions of BORIS).

The BORIS polypeptide can be joined to other biomolecules, such as, for example, proteins, polypeptides, lipids, carbohydrates, prenyl, and acyl moieties, and nucleic acids. Where another protein or polypeptide is linked with a portion of BORIS, it is preferably unrelated to BORIS (e.g., the other polypeptide will have less than 40% amino acid sequence identity with BORIS). In a preferred embodiment of the invention, the BORIS polypeptide comprises a flexible linker amino acid sequence. Flexible linkers are used in the art to join two distinct polypeptides, such as, for example, in the construction of fusion or chimeric proteins. In embodiments where the BORIS polypeptide comprises two or more portions of BORIS, for example, an N-terminal domain portion and a C-terminal domain portion of BORIS, a flexible linker can be used to join the N-terminal domain and the C-terminal domain to form a single polypeptide molecule. The flexible linker can be any suitable amino acid sequence that can be used to join to separate polypeptide domains. In this regard, the flexible linker preferably comprises about 5 or more amino acids (e.g., about 6 or more, 7 or more, or 9 or more amino acids), more preferably about 10 or more amino acids (e.g., about 11 or more, 12 or more, or 14 or more amino acids), and most preferably about 15 or more amino acids (e.g., about 17 or more, 20 or more, or 25 or more amino acids). The flexible linker for use in the present invention preferably comprises the amino acid sequence of SEQ ID NO: 5, however, other linker sequences as well as methods for joining polypeptide domains using flexible linkers are known in the art (see, e.g., Imanishi et al., *Biochem. Biophys. Res. Commun.*, 333(1), 167-73 (2005); Lin-et al., *Eur. Cytokine Netw.*, 15(3), 240-6 (2004)).

The BORIS polypeptide can be attached to a signaling moiety (also known as a detectable label). The identity and use of signaling moieties is well-known in the art. A signaling moiety is a molecule capable of indicating the presence of an analyte or reagent in a sample, usually after manipulation of the sample. Such manipulations often include incubating a sample and appropriate detection reagents under conditions allowing two moieties to bind together, if present, and then removing any of the labeled moiety from the sample via washing, filtration, or other suitable techniques. Other methods of working with signaling moieties are well-known in the art. Suitable signaling moieties include, but are not limited to, fluorescent molecules (e.g., green fluorescent protein), fluorescent quenchers, epitopes and haptens for antibodies that do not recognize BORIS (e.g., the well-known FLAG epitope), enzymes (e.g., chromogenic or luminescent (such as horse radish peroxidase or β-galactosidase)), a nucleic acid that can be amplified or specifically hybridized to a probe, biotin, avidin or streptavidin, lectins and colloids. Methods for linking proteins with detectable labels and solid supports are well-known in the art.

As the primary function of the BORIS polypeptide is to bind with anti-BORIS antibodies in the sample, the BORIS polypeptide need not comprise a portion of BORIS per se. Rather, the BORIS polypeptide can be a polypeptide that binds with an antibody that binds to BORIS. In this respect, the polypeptide can comprise, consist essentially of, or consist of a variant of BORIS. As used herein, the term "variant of BORIS" means a variant of the full-length native BORIS protein or a variant of a portion of BORIS, as described herein. The skilled artisan can generate and characterize BORIS variants for their ability to bind with an anti-BORIS antibody or a functional fragment thereof (e.g., a Fab or F'(ab)$_2$) using the information provided herein and routine methods known in the art. For example, BORIS variants can be generated using any suitable method known in the art, including, but not limited to, site-directed or random mutagenesis of a nucleic acid sequence encoding BORIS. The binding characteristics of a BORIS variant thus produced can be determined, for example, using antibodies to BORIS obtained from the serum of a mammal with cancer. Such antibodies can be obtained, for instance, using a native BORIS protein.

A variant of BORIS desirably shares one or more regions of amino acid sequence identity with a native BORIS protein. In this regard, the variant preferably comprises an amino acid sequence that is at least about 50% identical (e.g., at least about 60%, at least about 70%, at least about 80%, or at least about 90% identical) to a native BORIS polypeptide. More preferably, the polypeptide comprises an amino acid sequence that is at least about 75% identical (e.g., at least about 85%, or at least about 95% identical) to an amino acid sequence of native BORIS. Most preferably, the polypeptide comprises an amino acid sequence that is at least about 90% identical (e.g., at least about 95%, at least about 97%, or at least about 99% identical) to an amino acid sequence of native BORIS. As used herein, the sequence identity is that determined using the well-known BLAST algorithms (e.g., BLASTp, BLAST 2.1, BL2SEQ, and later versions thereof)). Variants of BORIS capable of binding to anti-BORIS antibodies preferably have at least 5, 6, or 7 amino acid residues that are identical to BORIS over a window of eight amino acid residues.

BORIS variants in which an alteration destroys the ability of the variant to bind with, or bind specifically with, an anti-BORIS antibody can be used as a negative control.

The antibody detected in the invention preferably binds to BORIS better than to CCCTC-binding-factor (CTCF), or does not bind CTCF at all. Thus, the method of the invention preferably comprises detecting an anti-BORIS antibody with a binding affinity for BORIS that is greater than its binding affinity for CTCF. This is particularly true where the portion of BORIS used comprises the zinc-finger domain of BORIS. More preferably, the dissociation constant ($K_d$) of binding under standard conditions between the antibody detected by the method of the invention and BORIS is at least 10-fold less, more preferably at least 100-fold less, or even 1000-fold less than the $K_d$ of binding between the same antibody and CTCF. In some embodiments, binding of antibodies in a patient's serum to CTCF can be used as a negative control.

The mammal used in conjunction with the methods described herein can be any suitable mammal, such as dogs, cats, cows, goats, pigs, mice, rats, guinea pigs, rabbits, gerbils, monkeys, and hamsters. The mammal preferably is a mouse, and more preferably a human.

The sample can be contacted with a BORIS polypeptide using any suitable method known in the art. Preferably, the sample is contacted with a BORIS polypeptide in vitro. In vitro methods for detecting antibodies in a sample are well known in the art and include, for example, enzyme-linked immunosorbent assay (ELISA), affinity chromatography, and radioimmunoassay (RIA).

In a preferred embodiment, the method of detecting cancer or method of detecting anti-BORIS antibodies includes determining the class and/or subclass of the antibodies present in the patient's body, or sample derived therefrom, that are reactive with BORIS. One of ordinary skill in the art will appreciate that the five major human immunoglobulin classes (or "isotypes") are immunoglobulin M (i.e., IgM), IgD, IgG, IgA, and IgE, which are typically defined by the structure of the constant regions of the antibody heavy chain. The light chain of a human antibody molecule is typically classified in the art as either a lambda ($\lambda$) chain or a kappa ($\kappa$) chain. IgG antibodies can be subdivided further into four subtypes (i.e., IgG1, IgG2, IgG3, and IgG4), whereas IgA antibodies typically are subdivided into two subtypes (i.e., IgA1 and IgA2). It is well-known in the art how to determine the class and subclass of isolated or purified antibodies. For example, BORIS-reactive antibodies can be isolated from a human's serum by immunochromatography. Wells of microtiter plates can be coated with 10 µg/ml of anti-human immunoglobin overnight at 4° C. After blocking with 5% BSA, the plates are reacted with 10 µg/ml of a monoclonal antibody or purified isotype controls, at ambient temperature for two hours. The wells can then be reacted with human IgG 1-specific, IgG2-specific, IgG3-specific or IgG4-specific or human IgM-specific alkaline phosphatase-conjugated probes. After washing, the plates can be developed with a luminogenic or chromogenic substrate and analyzed for light or color development.

The methods of detecting a disease and detecting anti-BORIS antibodies can be used in different ways. For example, the method can be used simply to establish the existence of a disease state for the purposes of diagnosis or screening. In addition, the method can be used, for example, to monitor the status (e.g., progression or regression) of a disease state, such as by comparing the level of anti-BORIS antibodies (or BORIS expression levels) from different samples over time. Such a use would be helpful in monitoring the response of patients to a particular therapeutic regimen.

The invention also provides an isolated immunoreactive portion of BORIS. By "immunoreactive portion" is meant a portion of the BORIS protein that can generate an immune response in a mammal in vivo, binds to an anti-BORIS antibody in vivo or in vitro, or comprises one or more BORIS epitopes. A portion of BORIS is isolated if it is synthesized, or if it is removed from its natural environment. The isolated immunoreactive portion of BORIS can comprise, consist essentially of, or consist of any portion of BORIS or any BORIS polypeptide described herein as useful in conjunction with the method of detecting a disease or method of detecting an anti-BORIS antibody, including without limitation the amino acid sequences encoded by any of SEQ ID NOs: 1-3.

The BORIS polypeptide or portion of BORIS, as described herein, can be generated using any suitable method. In this regard, nucleic acid sequences encoding BORIS fragments can be synthetically produced and expressed in an appropriate host cell, thereby resulting in production of a portion of a BORIS polypeptide. In addition, BORIS peptide fragments can be synthesized using protein synthesis methods known in the art. Alternatively, BORIS polypeptide fragments can be generated using proteases that cleave within the full-length BORIS polypeptide. As discussed above, the portion of BORIS can be labeled with a signaling moiety or detectable label, or linked to a solid support.

The invention further provides a composition comprising a BORIS polypeptide, as described herein, wherein the BORIS polypeptide can optionally be labeled with a detectable label. Ideally, the composition comprises a BORIS polypeptide and a pharmaceutically acceptable (e.g., physiologically acceptable) carrier, diluent, or excipient. The phrase "pharmaceutically acceptable carrier," as used herein, refers to a carrier medium which does not interfere with the effectiveness of the biological activity of the active ingredients and which is not toxic to the host or patient. The pharmaceutical compositions of the present invention can be in a variety of forms. These include, for example, solid, semi-solid and liquid dosage forms, such as tablets, pills, powders, liquid solutions or suspensions, liposomes, injectable and infusible solutions. Inhalable preparations, such as aerosols, are also included. Preferred formulations are those directed to oral, intranasal and parenteral applications, but it will be appreciated that the preferred form will depend on the particular diagnostic or therapeutic application. The methods for the formulation and preparation of pharmaceutical compositions are well known in the art and are described in, for example, *Remington's Pharmaceutical Sciences*, Mack Publishing Company, Philadelphia, Pa., 17th ed. (1985), *The Merck Index*, 11th ed., (Merck & Co. 1989), and Langer, *Science*, 249, 1527-1533 (1990).

The BORIS polypeptide as described herein, including a full-length native BORIS protein or isolated portions, fragments, chimeras, fusions, and derivatives thereof, can be used for any purpose. In addition to being useful in the method of detecting a disease and method of detecting anti-BORIS antibodies, the BORIS polypeptide can be used for other purposes, such as for inducing an immune response in a mammal. Such immune responses have multiple uses. For example, antibodies and other immunity-related molecules specific for BORIS can be isolated and used for research, control reagents useful in a method for detecting BORIS expression in a mammal, and as a method for destroying cancer cells that are present or could arise in a mammal. In this regard, the invention provides, as a related aspect, a method of inducing an immune response in a mammal comprising administering to a mammal a BORIS polypeptide as defined herein. Suitable methods of administration are known in the art. All other aspects of the method of inducing an immune response are as previously described herein.

A BORIS polypeptide as described herein, including a full-length native BORIS protein or isolated portions, fragments, chimeras, fusions, and derivatives thereof, can also be supplied in a kit. Thus, in a related aspect, the invention provides a kit comprising a BORIS polypeptide as described herein and a reagent that generates a signal when an antibody binds to a portion of a BORIS polypeptide. Such reagents are known in the art. The kit preferably further comprises instructions for determining whether a sample obtained from a mammal comprises antibodies specific for BORIS, which instructions optionally include criteria for determining whether a cancer cell is likely present in the mammal from which the sample was obtained. The kit can be used for any purpose, such as in researching BORIS expression and diseases associated therewith, and for the detection of BORIS antibodies and the detection of cancer in a mammal.

The following examples further illustrate the invention but, of course, should not be construed as in any way limiting its scope.

Example 1

This example demonstrates that indirect ELISA detection of serum antibodies to BORIS can be used to diagnose cancer in human patients.

In order to detect antibodies to BORIS present in human sera, an indirect ELISA was used, employing regions of BORIS that do not have homology to CTCF as bait. In this regard, three different plasmid constructs encoding portions of the N-terminal and/or C-terminal domains of BORIS were generated using the pGEX-5×1 plasmid (Amersham Biosciences, Piscataway, N.J.). The sequence of the full-length BORIS protein is provided in Loukinov et al., supra, Klenova et al., supra, and GenBank Accession No. AF336042. The first plasmid contained the N-terminal domain of BORIS corresponding to nucleotides 90-867 of the published BORIS nucleic acid sequence (GenBank Accession No. AF336042) and a flexible linker (SEQ ID NO: 5). The second plasmid contained the C-terminal domain of BORIS corresponding to nucleotides 1761-2098 of the published BORIS nucleic acid sequence. The third plasmid contained both the N-terminal domain and the C-terminal domain of BORIS of the second plasmid joined together via the flexible linker. Each BORIS sequence was expressed as part of a fusion protein with glutathione-5-transferase (GST) to facilitate purification.

Suitable concentrations (for example, about 1 μg/mL) of each of the BORIS fusion proteins in a suitable coating buffer (e.g., 15 mM $Na_2CO_3$, 30 mM $NaHCO_3$, pH 9.6 with 0.02% $NaN_3$) were absorbed onto 96-well microtititer plates for a suitable time and at a suitable temperature (e.g., overnight at 4° C.). Plates were then washed with a suitable solution (e.g., 0.05% Tween-20/PBS) and blocked (e.g., with 100 μl per well of a BSA or casein solution for about 1 hour at room temperature (RT)). After washing, serial dilutions of human serum in a suitable blocking reagent, such as BSA or casein, were added and incubated under suitable conditions (e.g., for about 2 hours at 37° C. in a water-saturated incubator). Serum was obtained from human patients suffering from glioma, lung cancer, breast cancer, and prostate cancer.

Plates were washed and diluted secondary antibody (including, e.g., anti-human IgG 1-specific, IgG2-specific, IgG3-specific, IgG4-specific or human IgM-specific alkaline phosphatase-conjugates) in a blocking agent was added and incubated for a suitable period of time under suitable conditions (e.g., about 1 hour at 37° C.) The plates were then washed, incubated with visualizing reagents under suitable conditions for suitable times, the reaction was stopped, and the results determined.

Using the BORIS fusion protein comprising the N-terminal domain linked to the C-terminal domain of BORIS, sera from forty seven cancer patients were positive for anti-BORIS antibodies, while sera from six normal humans were negative for anti-BORIS antibodies (see FIG. 1). FIG. 1 shows that the ELISA of the sera from six normal subjects had a mean microtiter plate reading of about 0.1. The sera from seventeen patients with gliomas had a mean microtiter plate reading of greater than 0.15, from nine patients with lung cancer a mean of about 0.3, from fifteen patients with breast cancer a mean of over 0.4, and from six patients with prostate cancer a mean of over 0.2. The differences between each cancer group's mean reading and that of normal human sera were statistically significant.

Antibodies to the N-terminal fragment of the BORIS fusion protein encoded by the first plasmid (e.g., without the C-terminal domain) were detected in human sera, but at lower levels than the antibodies specific to the BORIS polypeptide encoded by the third plasmid. Antibodies to the C-terminal fragment of the BORIS fusion protein encoded by the second plasmid (e.g., without the N-terminal domain) were not detectable.

This example demonstrates that the use of a BORIS polypeptide for the detection of anti-BORIS antibodies in serum is a highly specific method for the diagnosis of a wide variety of cancers.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A method of detecting a cancer characterized by abnormal BORIS expression in a mammal comprising detecting antibodies to a BORIS polypeptide in a sample obtained from the mammal, wherein the BORIS polypeptide comprises at least 100 amino acids of the amino acid sequence encoded by (a) SEQ ID NO: 1 or (b) SEQ ID NO: 2, and wherein the presence of antibodies to the BORIS polypeptide in the sample indicates the presence of the cancer in the mammal.

2. The method of claim 1, wherein the antibodies to BORIS are detected by
   (a) contacting the sample with a BORIS polypeptide comprising at least 100 amino acids of the amino acid sequence encoded by (a) SEQ ID NO: 1 or (b) SEQ ID NO: 2, and
   (b) detecting the binding of the BORIS polypeptide with an antibody.

3. The method of claim 1, wherein the cancer is breast cancer, glioma, lung cancer, or prostate cancer.

4. A method of detecting anti-BORIS antibodies in a sample from a mammal comprising:
   (a) contacting the sample with a BORIS polypeptide comprising at least 100 amino acids of the amino acid sequence encoded by (a) SEQ ID NO: 1 or (b) SEQ ID NO: 2, and
   (b) detecting the binding of the BORIS polypeptide with an antibody, wherein the binding of the BORIS polypeptide with the antibody indicates the presence of anti-BORIS antibodies in the sample.

5. The method of claim 1, wherein the mammal is a human.

6. The method of claim 1, wherein the sample is blood, serum, plasma, lymph, or interstitial fluid.

7. The method of claim 2, wherein the BORIS polypeptide comprises a full-length native BORIS polypeptide.

8. The method of claim 2, wherein the BORIS polypeptide comprises at least 200 amino acids of the amino acid sequence encoded by SEQ ID NO: 1.

9. The method of claim 8, wherein the BORIS polypeptide comprises the amino acid sequence encoded by SEQ ID NO: 1.

10. The method of claim 2, wherein the BORIS polypeptide comprises at least 100 amino acids of the amino acid sequence encoded by SEQ ID NO: 2.

11. The method of claim 10, wherein the BORIS polypeptide comprises the amino acid sequence encoded by SEQ ID NO: 2.

12. The method of claim 2, wherein the BORIS polypeptide further comprises a flexible linker.

13. The method of claim 12, wherein the flexible linker comprises an amino acid sequence of SEQ ID NO: 5.

14. The method of claim 2, wherein the BORIS polypeptide does not comprise the zinc-finger region of BORIS.

15. The method of claim 2, wherein the BORIS polypeptide comprises the amino acid sequence encoded by SEQ ID NO: 3.

16. The method of claim 2, further comprising determining the class of the antibody that binds with the BORIS polypeptide.

17. The method of claim 2, wherein the antibody detected has a binding affinity for BORIS that is greater than its binding affinity for CCCTC-binding-factor (CTCF).

18. The method of claim 4, wherein the mammal is a human.

19. The method of claim 4, wherein the sample is blood, serum, plasma, lymph, or interstitial fluid.

20. The method of claim 2 comprising contacting the sample with a BORIS polypeptide that comprises at least 200 amino acids from the N-terminal domain of BORIS of the amino acid sequence encoded by SEQ ID NO: 1.

21. The method of claim 2 comprising contacting the sample with a BORIS polypeptide that comprises the amino acid sequence encoded by SEQ ID NO: 1.

22. The method of claim 2 comprising contacting the sample with a BORIS polypeptide that comprises at least 100 amino acids from the C-terminal domain of BORIS of the amino acid sequence encoded by SEQ ID NO: 2.

23. The method of claim 2 comprising contacting the sample with a BORIS polypeptide that comprises the amino acid sequence encoded by SEQ ID NO: 2.

24. The method of claim 2 comprising contacting the sample with a BORIS polypeptide that further comprises a flexible linker.

25. The method of claim 24, wherein the flexible linker comprises an amino acid sequence of SEQ ID NO: 5.

26. The method of claim 2 comprising contacting the sample with a BORIS polypeptide that does not comprise the zinc-finger region of BORIS.

27. The method of claim 2 comprising contacting the sample with a BORIS polypeptide that comprises the amino acid sequence encoded by SEQ ID NO: 3.

28. The method of claim 2 comprising contacting the sample with a BORIS polypeptide that comprises a full-length native BORIS polypeptide.

* * * * *